US009695244B2

(12) United States Patent
Robblee et al.

(10) Patent No.: US 9,695,244 B2
(45) Date of Patent: Jul. 4, 2017

(54) METHODS RELATED TO DENOSUMAB

(71) Applicant: MOMENTA PHARMACEUTICALS, INC., Cambridge, MA (US)

(72) Inventors: John Robblee, Newton, MA (US); Brian Edward Collins, Arlington, MA (US); Ganesh Kaundinya, Bedford, MA (US); Carlos J. Bosques, Arlington, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/403,828

(22) PCT Filed: May 31, 2013

(86) PCT No.: PCT/US2013/043674
§ 371 (c)(1),
(2) Date: Dec. 1, 2014

(87) PCT Pub. No.: WO2013/181575
PCT Pub. Date: Dec. 5, 2013

(65) Prior Publication Data
US 2015/0246974 A1    Sep. 3, 2015

Related U.S. Application Data

(60) Provisional application No. 61/783,013, filed on Mar. 14, 2013, provisional application No. 61/654,515, filed on Jun. 1, 2012.

(51) Int. Cl.
A61K 39/00    (2006.01)
A61K 39/395   (2006.01)
C07K 16/28    (2006.01)
G01N 33/68    (2006.01)

(52) U.S. Cl.
CPC ..... C07K 16/2875 (2013.01); G01N 33/6854 (2013.01); C07K 2317/41 (2013.01); G01N 2440/38 (2013.01)

(58) Field of Classification Search
None
See application file for complete search history.

(56) References Cited

U.S. PATENT DOCUMENTS

| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Cryz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,551,730 A | 9/1996 | Barreca et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,667,984 A | 9/1997 | Parekh et al. |
| 5,679,321 A | 10/1997 | Dasgupta et al. |
| 5,712,254 A | 1/1998 | Chaki et al. |
| 5,723,583 A | 3/1998 | Seed et al. |
| 5,753,454 A | 5/1998 | Lee |
| 5,759,823 A | 6/1998 | Wong et al. |
| 5,856,143 A | 1/1999 | Nilsson |
| 5,879,912 A | 3/1999 | Roth |
| 5,945,322 A | 8/1999 | Gotschlich |
| 6,030,815 A | 2/2000 | DeFrees et al. |
| 6,048,707 A | 4/2000 | Klock, Jr. |
| 6,048,708 A | 4/2000 | Clausen et al. |
| 6,096,555 A | 8/2000 | Hermentin et al. |
| 6,132,994 A | 10/2000 | Tawada et al. |
| 6,149,954 A | 11/2000 | Merabet |
| 6,156,547 A | 12/2000 | Roth |
| 6,159,954 A | 12/2000 | Maruyama et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |
| 6,280,989 B1 | 8/2001 | Kapitonov et al. |
| 6,284,516 B1 | 9/2001 | Pollock et al. |
| 6,358,710 B1 | 3/2002 | Graves et al. |
| 6,597,996 B1 | 7/2003 | Venkataraman et al. |
| 7,364,736 B2 * | 4/2008 | Boyle .............. A61K 39/39541 424/133.1 |
| 8,034,906 B2 | 10/2011 | Borhani et al. |
| 8,524,217 B2 * | 9/2013 | Presta ................ C07K 14/4713 424/134.1 |
| 8,802,820 B2 | 8/2014 | Chamberlain et al. |
| 2002/0054878 A1 | 5/2002 | Lowman et al. |
| 2003/0157108 A1 | 8/2003 | Presta |
| 2004/0210396 A1 | 10/2004 | Fischer et al. |
| 2005/0054832 A1 | 3/2005 | Lazar et al. |
| 2006/0008415 A1 | 1/2006 | Kaisheva et al. |
| 2006/0040353 A1 | 2/2006 | Davidson et al. |

(Continued)

FOREIGN PATENT DOCUMENTS

JP    2002-542787 A    12/2002
JP    2005509403 A    4/2005

(Continued)

OTHER PUBLICATIONS

Reitman et al., "Mouse Lymphoma Cell Lines Resistant to Pea Letin are defective in Fucose Metabolism", J Biol Chem., vol. 255(20) pp. 9900-9906 (1980).

(Continued)

Primary Examiner — Shulamith H Shafer
(74) Attorney, Agent, or Firm — Choate, Hall & Stewart LLP; Rolando Medina; Stephanie L. Schonzwald

(57) ABSTRACT

The present invention relates to the characterization and production of denosumab.

20 Claims, 2 Drawing Sheets

(56) References Cited

U.S. PATENT DOCUMENTS

| | | |
|---|---|---|
| 2006/0127950 A1 | 6/2006 | Bosques et al. |
| 2006/0252672 A1 | 11/2006 | Betenbaugh et al. |
| 2008/0261301 A1 | 10/2008 | Kanda et al. |
| 2009/0041770 A1 | 2/2009 | Chamberlain et al. |
| 2009/0069232 A1 | 3/2009 | Callewaert et al. |
| 2009/0104603 A1 | 4/2009 | Satomaa et al. |
| 2009/0203550 A1 | 8/2009 | Venkataraman et al. |
| 2009/0220520 A1 | 9/2009 | Patell |
| 2009/0226968 A1 | 9/2009 | Betenbaugh et al. |
| 2009/0258014 A1 | 10/2009 | Laterra et al. |
| 2009/0311732 A1 | 12/2009 | Rossi et al. |
| 2009/0317834 A1 | 12/2009 | Laine et al. |
| 2010/0048456 A1 | 2/2010 | DeFrees et al. |
| 2010/0081150 A1 | 4/2010 | Liu et al. |
| 2010/0113294 A1 | 5/2010 | Venkataraman et al. |
| 2010/0129843 A1 | 5/2010 | Parsons et al. |
| 2010/0144553 A1 | 6/2010 | Bosques et al. |
| 2010/0173323 A1 | 7/2010 | Strome et al. |
| 2011/0136682 A1 | 6/2011 | Bosques et al. |
| 2011/0280873 A1 | 11/2011 | Presta et al. |
| 2012/0135461 A1 | 5/2012 | Cook et al. |
| 2015/0104444 A1 | 4/2015 | Robblee et al. |
| 2015/0125848 A1 | 5/2015 | Robblee et al. |
| 2015/0140608 A1 | 5/2015 | Robblee et al. |
| 2015/0141620 A1 | 5/2015 | Robblee et al. |
| 2015/0147317 A1 | 5/2015 | Robblee et al. |
| 2015/0152184 A1 | 6/2015 | Robblee et al. |
| 2015/0158943 A1 | 6/2015 | Robblee et al. |
| 2015/0204884 A1 | 7/2015 | Robblee et al. |
| 2015/0246974 A1 | 9/2015 | Robblee et al. |

FOREIGN PATENT DOCUMENTS

| | | | |
|---|---|---|---|
| WO | WO-9730087 A1 | 8/1997 | |
| WO | 0065070 A2 | 11/2000 | |
| WO | 0180884 A1 | 11/2001 | |
| WO | 0200879 A2 | 1/2002 | |
| WO | WO-02/061090 A2 | 8/2002 | |
| WO | WO-2004/065417 A2 | 8/2004 | |
| WO | 2005116221 A1 | 12/2005 | |
| WO | 2007011041 A1 | 1/2007 | |
| WO | 2007087384 A2 | 8/2007 | |
| WO | WO-2007/133855 A2 | 11/2007 | |
| WO | 2008063982 A2 | 5/2008 | |
| WO | 2008128228 A1 | 10/2008 | |
| WO | 2008128230 A1 | 10/2008 | |
| WO | 2008130926 A2 | 10/2008 | |
| WO | WO-2009/058492 A2 | 5/2009 | |
| WO | WO-2010/085251 A1 | 7/2010 | |
| WO | WO-2010/130756 A1 | 11/2010 | |
| WO | 2010136492 A2 | 12/2010 | |
| WO | 2010138502 A2 | 12/2010 | |
| WO | 2010141855 A1 | 12/2010 | |
| WO | 2011103584 A2 | 8/2011 | |
| WO | 2011127322 A1 | 10/2011 | |
| WO | 2011127325 A1 | 10/2011 | |
| WO | WO 2011/127322 * | 10/2011 | ............ C12Q 1/00 |
| WO | WO-2013/181585 A2 | 12/2013 | |
| WO | WO-2013/181586 A2 | 12/2013 | |

OTHER PUBLICATIONS

Restelli et al., "The effect of dissolved oxygen on the production and the glycosylation profile of recombinant human erythropoietin produced from CHO cells", Biotechnology and Bioengineering, 2006, vol. 94, No. 3, pp. 481-494.

Ripka et al., "Two Chinese Hamster Ovary Glycosylation Mutants Affected in the Converstion of GOP-Mannose to GOP-Fucose" Arch Biochem Biophys vol. 249(2) pp. 533-545 (1986).

Ritzenthaler et al., "Reevaluation of the effets of brefeldin A on plant cells using tobacco Bright Yellow 2 cells expressing Golgi-targeted green fluoresent protein and COPI antisera" Plant Cell, vol. 14(1) pp. 237-261 (2002).

Robinson D K et al: "Characterization of a recombinant antibody produced in the course of a high yield fed-batch process", Biotechnology and Bioengineering, Wiley & Sons, Hoboken, NJ, US, vol. 44, No. 6, 5, pp. 727-735 (1994).

Rodriguez J et al: "Enhanced production of monomeric interferon-[beta] by CHO cells through the control of culture conditions", Biotechnology Progress, American Institute of Chemical Engineers, US, vol. 21, No. 1, pp. 22-30 (2005).

Santell et al., "Aberrant metabolic sialylation of recombinant proteins expressed in Chinese hamster ovary cells in high productivity cultures", Biochemical and Biophysical Research Communications, 1999, vol. 258, pp. 132-137.

Sasaki et al., "Site-specific glycosylation of human recombinant erythropoietin: analysis of glycopeptides of peptides at each glycosylation site by fast atom bombardment mass spectrometry", Biochemistry, 1988, vol. 27, pp. 8618-8626.

Schulz et al., "Mediators of galactose sensitivity in UDP=galactoe 4'-epimerase-impaired mammalian cells" J. Biol Chem, 280 (14) pp. 13493-13502 (2005).

Schuster et al., "Improved effector functions of a therapeutic monoclonal Lewis V-specific antibody by glycoform engineering", Cancer Res., 2005, vol. 65, No. 17, pp. 7934-7941.

Search Report from Chinese Application No. 201180022319.9 dated Sep. 30, 2102.

Senger et al., "Effect of shear stress on intrinsic CHO culture state and glycosylation of recombinant tissue-type plasminogen activator protein", Biotechnol. Prog., 2003, vol. 19, pp. 1199-1209.

Serrato et al., "Heterogeneous conditions in dissolved oxygen affect N-glycosylation but not productivity of a monoclonal anitbody in hybridoma cultures", Biotechnology and Bioengineering, 2004, vol. 88, No. 2, pp. 176-188.

Shames et al., "CMP-N-acetylneuraminic acid synthetase of *Escherichia coli:* high level expression, purification and use in the enzymatic synthesis of CMP-N-acetylneuraminic acid and CMP-neuraminic acid derivatives", Glycobiology, 1991, vol. 1, pp. 187-191.

Sherman, MD, RE, Biosimilar Biological Products. Biosimilar Guidance Webinar. US Food and Drug Administration pp. 1-22 (2012).

Shinkawa eta l., The absense of fucose but not the presence of galactose or bisecting N-acetylglucosamine of human IgG1 complex-type oligosaccharides shows the critical role of enhancing antibody-dependent cellular cytotoxicity. J Biol Chem., vol. 278(5) pp. 3466-3473 (2003).

Sokolowski et al., "Conformational analysis of biantennary glycans and molecular moldeling of their complexes with lentil lectin", Journal of Molecular Graphics and Modeling, Feb. 1997, vol. 15, No. 1, pp. 37-42, 54, XP002293396 ISSN: 1093-3263.

Sparks et al., "Synthesis of potential inhibitors of hemagglutination by Influenza virus: chemoenzymic preparation of N-5 analogs of N-acetylneuraminic acid", Tetrahedron, 1993, vol. 49, pp. 1.

Spearman et al., "Production and glycosylation of recombinant ã-interferon in suspension and cytopore microcarrier cultures of CHO cells", Biotechnol. Prog., 2005, vol. 21, pp. 31-39.

Srinivas et al., "Pharmacokinetics and Pharmacodynamics of CTLA4Ig (BMS-188667), a Novel Immunosuppressive Agent, in Monkeys following Multiple Doses" Journal of Pharmaceutical Sciences, 85(1) pp. 1-4 (1996).

Srinivas et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats" Pharmaceutical Research, 14(7) pp. 911-916 (1997).

Sung et al., "Effect of sodium butyrate on the production, heterogeneity and biological activity of human thrombopoietin by recombinant Chinese hamster ovary cells", Journal of Biotechnology, 2004, vol. 112, pp. 232-335.

Supplemental Partial European Search Report, dated Aug. 31, 2004 for Application No. 02773390.6.

Takeuchi et al.,"Structures and functional roles of the sugar chains of human erythropoietins", Glycobiology, 1991, vol. 1, No. 4, pp. 337-346.

(56) References Cited

OTHER PUBLICATIONS

Tran et al., "Separation of carbohydrate-mediated microheterogeneity of recombinant human erythropoietin by free solution capillary electrophoresis", Journal of Chromatography, 1991, vol. 542, pp. 459-471.

Trombetta et al., "Glycoprotein reglucosylation and nucleotide sugar utlization in the secretory pathway: identification of a nucleoside diphosphatase in the endoplasmic reticulum" The EMBO Journal, vol. 18, No. 12, pp. 3282-3292 (1999).

Trummer et al., "Process parameter shifting: part I. Effect of DOT, pH, and temperature on the performance of Epo-Fc expressing CHO cells cultivated in controlled batch bioreactors", Biotechnol. and Bioeng., 2006, vol. 94, No. 6, pp. 1033-1044.

Umaña et al., "Engineered glycoforms of an antineuroblastoma IgG1 with optimized antibody-dependent cellular cytotoxic activity", Nature Biotechnology, 1999, vol. 17, pp. 176-180.

Van Berkel et al., "N-linked glycosylation is an important parameter for optimal selection of cell lines producing biopharmaceutical human IgG", Biotechnology Progress, Vo;. 25, No. 1, pp. 244-251 (2009).

Van De Nieuwenhof et al., "Recombinant glycodelin carring the same type of glycan structures as contraceptive glycodelin-A can be produced in human kidney 293 cells but not in Chinese hamster ovary cells" Eur. J. Biochem, vol. 267 pp. 4753-4762 (2000).

Varki, "Radioactive tracer techniques in the sequencing of glycoprotein oligosaccharides", J. FASEB, 1991, vol. 2, pp. 226-235.

Venkataraman et al., "Sequencing complex polysaccharides", Science, 1999, vol. 286, pp. 537-542.

Von Der Lieth, "Expanding proteomics to glycobiology: biocomputing approaches understanding the function of sugar", Pacific Symposium on Biocomputing, 2002, Abstract.

Wang et al., "EDEM an ER quality control receptor" Nat. Struct. Biol., vol. 10(5) pp. 319-321 (2003).

Watson et al.,"Capillary electrophoresis separation of human recombinant erythropoietin (r-HuEPO) glycoforms", Analytical Biochemistry, 1993, vol. 210, pp. 389-393.

Watson et al.,"Structure determination of the intact major sialylated oligosaccharide chains of recombinant human erythropoietin expressed in Chinese hamster overy cells", Glycobiology, 1994, vol. 4, No. 2, pp. 227-237.

Webb J W et al., Structural characterization of intact, branched oligosaccharides by high performance liquid chromatography and liquid secondary ion mass spectrometry Analytical Biochemistry, vol. 169, pp. 337-349 (1998).

Weiner et al., "A senstive enzyme immunoassay for the quantitation of human CTLA4Ig fusion proten in mouse serum: pharmacokinetic application to optimizing cell line selection" Journal of Pharmaceutical and Biomedical Analysis, 15(5) pp. 571-579 (1997).

Wong et al., "Impact of dynamic online fed-batch strategies on metabolism, productivity and N-glycosylation quality in CHO cell cultures", Biotechnol. and Bioeng., 2005, vol. 89, No. 2, pp. 164-177.

Wopereis et al., "Mechanisms in Protein O-Glycan Biosynthesis and Clinical and Molecular Aspects of Protein O-Glycan Biosynthesis Defects: A Review" Clinical Chem., vol. 52(4) pp. 547-600 (2006).

Wright et al., "In vivo trafficking and catabolism of IgG1 antibodies with Fc associated carbohydrates of differing structure", Glycobiology, 2000, vol. 10, No. 12, pp. 1347-1355.

Yang et al. "Bio-Basis Function Neural Network for Prediction of Protease Cleavage Sites in Proteins" IEEE Transactions on Neural Netwroks, vol. 16, pp. 263-274 (2005).

Yang et al., "Achievement of high cell density and high antibody productivity by a controlled-fed perfusion bioreactor process", Biotechnol. and Bioeng., 2000, vol. 69, No. 1, pp. 74-82.

Yang et al., "Effect of ammonia on the glycosylation of human recombinant erythropoietin in culture", Biotechnol. Prog., 2000, vol. 16, pp. 751-759.

Ye et al., "N-glycan branching requirement in neuronal and postnatal viability", Glycobiology, vol. 14(6) pp. 547-558 (2004).

Yoon et al., "Effect of culture pH on erythropoietin production by Chinese hamster overy cells grown in suspension at 32.5 and 37 degree Celsius", Biotechnol. and Bioeng., 2005, vol. 89, No. 3, pp. 345-356.

Yoon et al., "Effect of simultaneous application of stressful culture conditions on specific productivity and heterogeneity of erythropoietin in Chinese hamster overy cells", Biotechnol. Prog., 2004, vol. 20, pp. 1293-1296.

Yuen et al., "Relationships between the N-glycan structures and biological activities of recombinant human erythropoietins produced using different culture conditions and purification procedures", British Journal of Haematology, 2003, vol. 121, pp. 511-526.

Yuk et al., "Changes in the overall extent of protein glycosylation by Chinese hamster overy cells over the course of batch culture", Biotechnol. Appl. Biochem., 2002, vol. 36, pp. 133-140.

Yuk et al., "Glycosylation by Chinese hamster overy cells in dolichol phosphate-supplemented cultures", Biotechnol. Appl. Biochem., 2002, vol. 36, pp. 141-147.

Ahn et al, "Separation of 2-aminobenzamide labeled glycans using hydrophilic interaction chromatography columns packed with 1.7⁻m sorbent" Journal of Chromatography B (2010) 878 pp. 403-408.

Chelius et al., "Formulation of Pyroglutamic Acid from N-Terminal Glutamic Acid in Immunoglobulin Gamma Antibodies" Analytical Chemistry (2006) vol. 78 No. 7 pp. 2370-2376.

Chen et al. "Gas-Phase Oligosaccharide Nonreducing End (GONE) Sequencing and Structural Analysis by Reversed Phase HPLC/Mass Spectrometry with Polarity Switching" J Am Soc Mass Spectrom (2009) vol. 20 pp. 1821-1833.

Chen et al., "Analysis of N-glycans from recombinant immunoglobulin G by on-line reversed-phase high-performance liquid chromatography/mass spectrometry" Analytical Biochemistry (2007) vol. 370 pp. 147-161.

Chumsae et al. "Identification and Localization of Unpaired Cysteine Residues in Monoclonal Antibodies by Fluorescence Labeling and Mass Spectrometry" Analytical Chemistry (2009) vol. 81 No. 15 pp. 6449-6457.

Dick et al. "C-Terminal Lysine Variants in Fully Human Monoclonal Antibodies: Investigation of Test Methods and Possible Causes" Biotechnology and Bioengineering (2008) vol. 100 No. 6 pp. 1132-1143.

Extended European Search Report from EP13878846.8 mailed Oct. 22, 2015.

FDA Guidance "Quality Considerations in Demonstrating Biosimilarity to a Reference Protein Product" (Feb. 2012, p. 1-22).

FDA Guidance Scientific Considerations in Demonstrating Biosimilarity to a Reference Product (Feb. 2012, p. 1-17).

Forrer et al., "Chip-based gel electrophoresis method for the quantification of half-antibody species in IgG4 and their by- and degradation products" Analytical Biochemistry (2004) vol. 334 pp. 81-88.

Goetze et al. "High-mannose glycans on the Fc region of therapeutic IgG antibodies increase serum clearance in humans" Glycobiology (2011) vol. 21 No. 7 pp. 949-959.

Hokke et al. "Sialylated carbohydrate chains of recombinant human glycoproteins expressed in Chinese hamster ovary cells contain traces of N-glycolylneuraminic acid" FEBS Letters (1990) vol. 275 No. 1, 2 pp. 9-14.

Miller et al., "Characterization of Site-Specific Glycation During Process Development of a Human Therapeutic Monoclonal Antibody" Journal of Pharmaceutical Sciences (2011) vol. 100 No. 7 pp. 2543-2549.

Shang et al. "Development and Application of a Robust N-Glycan Profiling Method for Heightened Characterization of Monoclonal Antibodies and Related Glycoproteins" Journal of Pharmaceutical Sciences (2014) vol. 103 pp. 1967-1978.

Stadlmann et al., "Analysis of immunoglobulin glycosylation by LC-ESI-MS of glycopeptides and oligosaccharides" Proteomics (2008) vol. 8 pp. 2858-2871.

Wang et al. "Characterization and Comparison of Disulfide Linkages and Scrambling Patterns in Therapeutic Monoclonal Antibod-

(56) References Cited

OTHER PUBLICATIONS ies: Using LC-MS with Electron Transfer Dissociation" Analytical Chemistry (2011) vol. 83 pp. 3133-3140.
Xie et al. "Rapid comparison of a candidate biosimilar to an innovator monoclonal antibody with advanced liquid chromatography and mass spectrometry technologies" mAbs—Landes Bioscience (2010) vol. 2 No. 4 pp. 379-394.
Yan et al. "Analysis of post-translational modifications in recombinant monoclonal antibody IgG1 by reversed-phase liquid chromatography/mass spectrometry" J. Chromatogr. A (2007) vol. 1164 pp. 153-161.
Akiyama et al., "Analysis of the role of glycosylation of the human fibronectin receptor", J. Biol. Chem. vol. 264(30) pp. 18011-18018 (1989).
Andersen et al., "Multiple cell culture factors can affect the glycosylation of Asn-184 in CHO-produced tissue-type plasminogen activator", Biotechnol. Bioeng., 2000, vol. 70, pp. 25-31.
Andrade et al., "Solid-phase oligosaccharide synthesis: preparation of comlex structures using a novel linker and different glycosylating agents", Org. Lett., 1999, vol. 1, No. 11, pp. 1811-1814.
Anulula et al., "Advances in fluorescence derivatization methods for high-performance liquid chromatographic analysis of glycoprotein carbohydrates", Analytical Biochemistry, 305(1), pp. 1-23 (2006).
Baker et al., "Metabolic control of recombinant protein N-glycan processing in NSO and CHO cells", Biotechnol. Bioeng., 2001, vol. 73, pp. 188-202.
Becker et al., "Fucose: biosynthesis and biological function in mammels" Glycobiology, Jul. 13(7) pp. 41R-53R (2003).
Bohne et al., "Sweet-WWW-based rapid 3D construction of oligo- and polysaccharides", Bioinformatics, Sep. 1999, vol. 15, No. 9, pp. 767-768, XP 001024942 ISSN: 1367-4803, Oxford University Press, Surrey, GB.
Bollati-Foglin et al., "Temperature reduction in cultures of hGM-CSF-expressing CHO cells: effect on productivity and product quality", Biotechnol. Prog., 2005, vol. 21, pp. 17-21.
Bowman et al., "Biosynthesis of L-selectin ligands: sulfation of sialyl Lewis x-related oligosaccharides by a family of GlcNAc-6-sulfotransferases", Biochemistry, 2001, vol. 40, No. 18, pp. 5382-5391.
Breidenbach et al., "Targeted metabolic labeling of yeast N-glycans with unnatural sugars" Proc. Natl. Acad. Sci., vol. 107(9) pp. 3988-3993 (2010).
Broschat et al., "Purification and characterization of GDP-D-mannose 4,6-dehydratase from porcine", Thyroid. Eur. J. Biochem., 1985, vol. 153, No. 2, pp. 397-401.
C.E. Joosten et al: "Effect of Culture Conditions on the Degree of Sialylation of a Recombinant Glycoprotein Expressed in Insect Cells", Biotechnology Progress, vol. 19, No. 3, 6 pp. 739-749 (2003).
Cabrera et al., "Influence of culture conditions of the N-glycosylation of a monoclonal antibody specific for recombinant hepatitis B surface antigen", Biotechnol. Appl. Biochem., 2005, vol. 41, pp. 67-76.
Chen et al., "Independent Lec1A CHO Glycosylation Mutants Arise from Point Mutations in N-Acetylglucosaminyltransferase I that Reduce Affinity for Both Substrates. Molecular Consequences Based on the Crystal Structure of GlcNac-TI", Biochemistry vol. 40(30) pp. 8765-8772 (2001).
Chen et al., "T cell receptors signaling co-regulates multiple Golgi genes to enhance N-glycan branching" J. Boil. Chem. vol. 284(47) pp. 32454-32461 (2009).
Chen P et al: "Effects of elevated ammonium on glycosylation gene expression in CHO cells", Metabolic Engineering, Academic Press, US, vol. 8, No. 2, pp. 123-132 (2006).
Clark et al., "Gene-expression profiles for five key glycosylation genes for galactose-fed CHO cells expression recombinant IL-4/13 cytokine trap", Biotechnol. and Bioeng., 2005, vol. 90, No. 5, pp. 568-577.
Cooper et al., "GlycoSuiteDB: a curated relational database of glycoprotein glycan structures and their biological sources. 2003 update", Nucleic Acids Research, 2003, vol. 31, No. 1, pp. 511-513.
Cooper et al., "GlycoSuiteDB: a new curated relational database of glycoprotein glycan structures and their biological sources", Nucleic Acids Research, 2001, vol. 29, No. 1, pp. 332-335.
Cox et al: "Glycan Optimization of a Human Monoclonal Antibody in the Aquatic Plant Lemna Minor", Nature Biotechnology, Nature Publishing Group, New York, NY, US, vol. 24, No. 12, pp. 1591-1597 (2006).
Crowell et al., "Amino acid and manganese supplementation modulates the glycosylation state of erythropoietin in a CHO culture system", Biotechnol. and Bioeng., 2006, pp. 538-549.
Debray et al, "Glycoprotein Analysis: General Methods", In: "Encyclodpedia of Analytical Chemistry" pp. 1-39.
Donaldson et al., "The use of lectins to select subpopulations of insect cells", Biotechnol. and Bioeng., 1999, vol. 61, pp. 616-619.
Dorka et al., "Modelliong Batch and Fed-Batch Mammalian Cell Cultures for Optimizing MAb Productivity", M.S. Thesis pp. 1-197 (2007).
Drecktrah et al., "Inhibition of a Golgi complex lysophospholipid acyltransferase induces membrane tuble formation and retrograde trafficing" Mol. Biol. Cell, vol. 14(8) pp. 3459-3469 (2003).
European Patent Office, Communication pursuant to Article 96(2) mailed Oct. 30, 2007 in related European Patent Application No. 02 773 390.6.
Extended European Search Report dated Mar. 1, 2013.
Extended European Search Report from European Application No. 11766759.2 dated Aug. 19, 2013.
Extended European Search Report from European application serial No. 11766762.6 dated Jan. 28, 2014.
Fareed, "S-9-10 synthetic and biotechnology derived glycomimetics", Impact on Drug Development, 2000, Database Google 6th Annual Pg Forum, Abstract.
FDA. Scientific Considerations in Demonstrating Biosimilarity to a Reference Product [online] Feb. 2012 [retrieved Dec. 10, 2013].
Ferrara et al., "Modulation of therapeutic antibody effector functions by glycosylation engineering: influence of golgi enzyme localization domain and co-expression of heterologous b 1, 4-N-acetylglucosaminyltransferase III and golgi a-mannosidase II", Biotechnol. and Bioeng., 2006, vol. 93, No. 5, pp. 851-861.
Fitz et al., "Combined use of subtilisin and N-acetyl neuraminic acid aldolase for the synthesis of a fluorescent sialic acid", J. Org. Chem., 1994, vol. 59, pp. 8279.
Fleischer eta l., "Mechanism of Glycosylation ion the Golgi Apparatus" The Journal of Histochemistry and Cytochemistry, vol. 31, No. 8, pp. 1033-1040 (1983).
Forno et al., "N- and O-linked carbohydrates and glycosylation site occupancy in recombinant human granulocytemacrophage colony-stimulating factor secreted by a Chinese hamster overy cell line", Eur. J. Biochem., 2004, vol. 271, pp. 907-919.
Fukuda et al., "Survival of recombinant erythropoietin in the circulation: the role of carbohydrates", Blood, 1989, vol. 73, pp. 84-89.
Gates et al., "Glycoprotein analysis manual" internet citation, pp. 1-89, retrieved from the Internet:URL:download.bioon.com.cn/view/upload/201301/27194411_2997.pdf.
Gawlitzek et al., "Ammonium alters N-glycan structures of recombinant TNFR-IgG: degradative versus biosynthetic mechanisms", Biotechnol. and Bioeng., 2000, vol. 68, No. 6, pp. 637-646.
Gawlitzek et al., "Characterization of changes in the glycosylation pattern of recombinant proteins from BHK-21 cells due to different culture conditions", Journal of Biotechnology, 1995, vol. 42, pp. 117-131.
Goldman et al., "Monitoring recombinant human interferon-g N-glycosylation and during perfused fluidized-bed and stirred-tank batch culture of CHO cells", Biotechnol. and Bioeng., 1998, vol. 60, pp. 596-607.
Gu et al., "Improvement of interferon-g sialylation in Chinese hamster ovary cell culture by feeding of N-acetylmannosamine", Biotechnol. and Bioeng., 1998, vol. 58, pp. 642-648.

(56) References Cited

OTHER PUBLICATIONS

Hara et al., "Determination of Mono-O-acetylated N-Acetylneuraminic Acids in Human and Rat Sera by Fluorometric High-Performance Liquid Chromatography" Analytical Biochemistry, 179 pp. 162-166 (1989).

Harue Imai-Nishiya et al., "Double knockdown of a 1,6 fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnology, 2007, vol. 7, No. 84, pp. 1-13.

Hendrick V et al: "Increased productivity of recombinant tissular plasminogen activator (t-PA) by butyrate and shift of temperature: a cell cycle phases analysis", Cytotechnology, Kluwer Academic Publishers, DO, vol. 36, No. 1-3, pp. 71-83 (2001).

Hewitt et al., "Solution and solid-support synthesis of a potential leishmaniasis carbohydrate vaccine", J. Org. Chem., 2001, vol. 15, No. 66(12), pp. 4233-4243.

Hills et al., "Metabolic control of recombinant monoclonal antibody N-glycosylation in GS-NSO cells", Biotechnol. and Bioeng., 2001, vol. 75, pp. 239-251.

Hirabayashi et al., "Separation technologies for glycomics", J. Chromatog. B Analyst. Biomed. Life Sci., May 2002, vol. 771, No. 1-2, pp. 67-87, Database Medline, US National Library of Medicine, Abstract.

Hoja-Lukowicz et al., "High-mannose-type oligosaccharides form human placental arylsulfatase A are core fucosylated as confirmed bu MALDI MS", Gyclobiology, vol. 10, No. 6, pp. 551-557 (2000).

Hosoi S et al: "Modulation of Oligosaccharide Structure of a Pro-Urokinase Derivative (PRO-UKDELTAGS1) by Changing Culture Conditions of a Lymphoblastoid Cell Line Namalwa KJM-1 Adapted to Serum-Free Medium", Cytotechnology, Kluwer Academic Publishers, Dordrecht, NL, vol. 19, No. 2, pp. 125-135 (1996).

Hossler et al., "Systems analysis of N-glycan processing in mammalian cells" PLoS One, vol. 2(8)e713 pp. 1-17 (2007).

International Preliminary Report on Patenability including the Written Opinion from International Application Serial No. PCT/US2010/036058 mailed Nov. 19, 2010.

International Preliminary Report on Patentability for International Application No. PCT/US2011/031637 mailed Oct. 18, 2012.

International Preliminary Report on Patentability for International Application Serial No. PCT/US2012/028759 issued Jan. 14, 2014.

International Preliminary Report on Patentability from PCT Application Serial No. PCT/US2008/060354 mailed Apr. 2, 2009.

International Preliminary Report on Patentability including the Written Opinion for International Application Serial No. PCT/US2011/031641 mailed Aug. 17, 2011.

International Search Report and Written Opinion for corresponding International Application Serial No. PCT/US2011/31637 mailed Aug. 30, 2011.

International Search Report and Written Opinion for corresponding International Application Serial No. PCT/US2013/043670 mailed Jan. 7, 2014.

International Search Report and Written Opinion from International Serial No. PCT/US13/43696 mailed Jan. 17, 2014.

International Search Report dated Jan. 7, 2014 in PCT/US2013/43671.

International Search Report for PCT/US2002/29285 filing date Dec. 23, 2002.

International Search Report for PCT/US2004/04423, mailed Dec. 28, 2004.

International Search Report for PCT/US2010/36058, dated Nov. 19, 2010.

International Search Report for PCT/US2010/37454, dated Sep. 1, 2010.

International Search Report including the Written Opinion for International Application Serial No. PCT/US2013/043667 mailed Jan. 13, 2014.

International Search Report including Written Opinion for International Application Serial No. PCT/US13/43676 mailed Jan. 16, 2014.

International Search Report including Written Opinion for PCT/US13/43671 mailed Jan. 7, 2014.

International Search Report including Written Opinion for PCT/US2012/28759 mailed Sep. 4, 2012.

International Search Report including Written Opinion for PCT/US2013/43674 mailed Jan. 15, 2014.

International Search Report including Written Opinion for PCT/US2013/43675 mailed Dec. 23, 2013.

Jabs et al. Fast and Extensive Mass Spectrometry Characterization of Theraputic mABs: The Panitumumab Case Study [online] CASSS Mass Spec Meeting Sep. 14, 2012 Poster 125 [ retrieved Dec. 10, 2013].

Jong Hyun Nam et al: "The effects of culture conditions on the glycosylation of secreted human placental alkaline phosphatase produced in Chinese hamster ovary cells", Biotechnology and Bioengineering, vol. 100, No. 6, 4, pp. 1178-1192 (2008).

Kakehi et al., "Analysis of glycoproteins, glycopeptides and glycoprotein-derived polysaccharides by high-performance capillary electrophoresis", J. Chromatogr. A., 1996, vol. 720, No. 1-2, pp. 377-393.

Kanda et al., "Comparison of biological activity among nonfucosylated therapeutic IgF1 antibodies with three different N-linked Fc oligosaccharides: the high-mannose, hybride, and complex types" Glycobiology, vol. 17(1) pp. 104-118 (2007).

Kanda et al., "Establishment of a GDP-mannose 4,6-dehydratase (GMD) knockout host cell line: A new strategy for generating completely non-cucosylated recombinant therapeutics" Journal of Biotechnology, vol. 130 pp. 300-310 (2007).

Kawashima et al., "Tyrosine kinase activity of epidermal growth factor receptor is regulated by GM3 binding through carbohydrate to carbohydrate interactions" J. Biol. Chem. vol. 284(10) pp. 6147-6155 (2009).

Keiser et al., "Direct isolation and sequencing of specific protein-binding glycosaminoglycans", Nature Medicine, 2001, vol. 7, No. 1, pp. 123-128.

Keppler et al., "Biosynthetic modulation of sialic acid-dependent virus-receptor interactions of two primate polyoma viruses", J. Biol. Chem., 1995, vol. 270, No. 3, pp. 1308-1314.

Kim et al., "Production and N-glycan analysis of secreted human erythropoietin glycoprotein in stably transfected *Drosophilia* S2 cells", Biotechnol. and Bioeng., 2005, vol. 92, No. 4, pp. 452-461.

Kosa et al., "Modification of cell surfaces by enzymetic introduction of special sialic acid analogues", Biochm. Biophys. Res. Commun., 1993, vol. 190, pp. 914.

Krapp et al., "Structural Analysis of Human IgG-Fc Glycoforms Reveals a Correlation Between Glycosylation and Structural Integrity", Journal of Molecular Biology, 325(5) pp. 979-989 (2003).

Kunkel et al., "Comparisons of the glycosylation of a monoclonal antibody produced under nominally identical cell culture conditions in two different bioreactors", Biotechnol. Prog., 2000, vol. 16, pp. 462-470.

Kunkel et al., "Dissolved oxygen concentration in serum-free continuous culture affects N-linked glycosylation of a monoclonal antibody", Journal of Biotechnology, 1998, vol. 62, pp. 55-71.

Le Floch et al., "HPCE monitoring of the N-glycosylation pattern and sialylation of murine erythropoietin produced by CHO cells in batch processes", Biotechnol. Prog., 2004, vol. 20, pp. 864-871.

Lifely M R et al: "Glycosylation and biological-activity of CAMPATH-1H expressed in different cell-lines and grown under different culture conditions", Glycobiology, Oxford University Press, US, vol. 5, No. 8, pp. 813-822 (1995).

Lin et al., "Unusual stereoselectivity in sialic acid aldolase-catalyzed aldol condensations: synthesis of both enantiomers of high-carbon monosaccharides", J. Am. Chem. Soc., 1992, vol. 114, pp. 10138-10145.

Lipscomb et al., "Effect of production method and gene amplification on the glycosylation pattern of a secreted reporter protein in CHO cells", Biotechnol. Prog., 2005, vol. 21, pp. 40-49.

Live et al., "Conformational influences of a glycosylation of a peptide: a possible model for the effect of glycsylation on the rate

(56) References Cited

OTHER PUBLICATIONS of protein folding", Proceedings of the National Academy of Sciences of the United States of America, 1996, vol. 93, No. 23, pp. 12759-12761, XP002293395 ISSN: 0027-8424.
Lopez-Avalos et al., "The UDPase activity of the Kluyveromyces lactis Golgi GDPase has a riole in uridine nucleotide sugar transport into Golgi vesicles", Glycobiology, vol. 11(5) pp. 413-422 (2001).
MacMillan et al.,"Selective in vitro glycosylation of recombinant proteins: semi-synthesis of novel homogeneous glycoforms of human erythropoietin", Chemistry and Biology, 2001, vol. 8, pp. 133-145.
Moran et al., "A systematic approach to the validation of process control parameters for monoclonal antibody production in fed-batch culture of a murine myeloma", Biotechnol. and Bioeng., 2000, vol. 69, No. 3, pp. 242-255.
Mueller et al., "Recombinant glycoprotein product quality in proliferation-controlled BHK-21 cells", Biotechnol. and Bioeng., 1999, vol. 65, No. 5, pp. 529-536.
Nairn et al., "Regulation of glycan structures in animal tissues: transcript profiling of glycan-related genes" J. Biol. Chem., vol. 282(25) pp. 17298-17313 (2008).
Zhang et al., "Quantitative analysis and process monitoring of site-specific glycosylation microheterogeneity in recombinant human interferon-gamma from Chinese hamster ovary cell culture by hydrophilic interaction chromatography" Journal of Chromatography B: Biomedical Sciences & Applications, vol. 712, No. 1-2, pp. 73-82 (1998).
Itoh, S. et al., Structural analysis of a glycoprotein by liquid chromatography-mass spectrometry and liquid chromatography with tandem mass spectrometry—Application to recombinant human thrombomodulin, Journal of Chromatography, 978(1-2): 141-152 (2002).
Anumula, KR., New high-performance liquid chromatography assay for glycosyltransferases based on derivatization with anthranilic acid and fluorescence detection, Glycobiology, 22(7):912-917 (2012).
Author Not Known, Glycosylation main approval issue with biosimilars, Generics and Biosimilars Initiative, 4 pages (2009).
Author Not Known, Guidance for Industry: Scientific Considerations in Demonstrating Biosimilarity to a Reference Product, Center for Biologics Evaluation and Research (CBER), Food and Drug Administration, 25 pages (2012).
Author Not Known, Rituxan Product Label, Biogen and Genentech, 35 pages (2010).
Author Not Known, Third Party Observation, filed in EP 13796989.5 (EP 2856158 A2), 16 pages (Jun. 9, 2016).
Ghaderi, D. et al., Production platforms for biotherapeutic glycoproteins. Occurrence, impact, and challenges of non-human sialylation, Biotechnology and Genetic Engineering Reviews, 28(1):147-176 (2012).
Greer, Fiona, Biosimilars Developers Face a Reference-Product Dilemma, BioPharm International, 3 pages (2012).
Hincal, Filiz, An Introduction to Safety Issues in Biosimilars/Follow-on Biopharmaceuticals, J Med CBR Def, 7: 18 pages (2009).
International Search Report from PCT Application Serial No. PCT/US2008/060354 mailed Jul. 16, 2009.
International Search Report from PCT/US13/43710, 5 pages (Jan. 3, 2014).
International Search Report from PCT/US2013/043671, 6 pages (Jan. 7, 2014).
International Search Report including the Written Opinion for International Application Serial No. PCT/US2011/031641 mailed Aug. 17, 2011.
International Search Report including Written Opinion for International Application Serial No. PCT/US13/43693 mailed Jan. 13, 2014.

Kalodiki, E. and Fareed, J., New and Generic Anticoagulants and Biosimilars: Safety Considerations, Clinical and Applied Thrombosis/Hemostasis, 5 pages (2010).
Kronewitter et al., The development of retrosynthetic glycan libraries to profile and classify the human serum N-linked glycome, Proteomics 2009, 9, 2986-2994.
Lattova, E. et al., Alterations in Glycopeptides Associated with Herceptin Treatment of Human Breast Carcinoma MCF-7 and T-Lymphoblastoid Cells, Molecular & Cellular Proteomics, 10: 12 pages (2011).
Ledford, Heidi. 'Biosimilar' drugs poised to penetrate market, Nature News, 468:18-19 (2010).
Ma et al., Carbohydrate analysis of a chimeric recombinant monoclonal antibody by capillary electrophoresis with laser-induced fluorescence detection, Anal. Chem., 71(22): 5185-5192 (1999).
Misra, Anoop, Are biosimilars really generics?, Expert Opin. Bio. Ther., 10(4):489-494 (2010).
Nowicki, Michal, Basic Facts about Biosimilars, Kidney & Blood Press Res, 30:267-272 (2007).
Presta, L.G. et al., Humanization of an anti-vascular endothelial growth factor monoclonal antibody for the therapy of solid tumors and other disorders, Cancer Research, 57(20):4593-4599 (1997).
Rader, Ronald A., Nomenclature of New Biosimilars Will Be Highly Controversial, BioProcess International, pp. 26-33 (2011).
Roger, Simon D., Biosimilars: current status and future directions, Expert Opin. Biol. Ther., 10(7):1011-1018 (2010).
Schellekens, H. and Moors, E., Clinical comparability and European biosimilar regulations, Nature Biotechnology, 28(1):28-31 (2010).
Schellekens, Huub, Biosimilar therapeutics—what do we need to consider?, NDT Plus, 2(Suppl 1):127-136 (2009).
Schiestl, M. et al., Acceptable changes in quality attributes of glycosylated biopharmaceuticals, Nature Biotechnology, 4:310-312 (2011).
Sekhon, B. and Saluja, V., Biosimilars: an overview, Biosimilars, 1:1-11 (2011).
Tan, Q. et al., Characterization and comparison of commercially available TNF receptor 2-Fc fusion protein, mAbs, 4(6):761-774 (2012).
Townsend, R., Analysis of Glycoconjugates Using High-pH Anion-Exchange Chromatography, Journal of Chromatography Library, 58:181-209 (1995).
Written Opinion from PCT/US13/43710, 12 pages (Jan. 3, 2014).
Zhang, N. et al., Glycoengineered Pichia produced anti-HER2 is comparable to trastuzumab in preclinical study, mAbs, 3(3):289-298 (2011).
Nyberg et al ., "Metabolic effects on recombinant interferon-g glycosylation in continuous culture of Chinese hamster ovary cells", Biotechnol. and Bioeng., 1999, vol. 62, No. 3.
Oh et al.,"Effect of N-acetylcystein on butyrate-treated Chinese hamster overy cells to improve the production of recombinant human interferon-b-1a", Biotechnol. Prog., 2005, vol. 21, pp. 1154-1164.
Pace et al., "Characterization of Minor N-linked Glycans on Antibodies Using Endo H Release and MALDI-Mass Spectrometry" Analytical Letters, vol. 42, No. 11, pp. 1711-1724 (2009).
Park et al., "Expression of carbamoyl phosphate synthetase I and ornithine transcarbamoylase genes in Chinese hamster ovary dhfr-cells decreases accumulation of ammonium ion in culture media", Journal of Biotechnology, 2000, vol. 81, pp. 129-140.
Plante et al., "Automated solid-phase synthesis of oligosaccharides", Science, 2001, vol. 291, No. 5508, pp. 1523-1527.
Plante et al., "Formation of b-glucosamine and b-mannose linkages using glycosyl phosphates", Org. Lett., 2000, vol. 2, No. 24, pp. 3841-3843.

\* cited by examiner

FIG. 1

Denosumab HC sequence (SEQ ID NO:1):

EVQLLESGGGLVQPGGSLRLSCAASGFTFSSYAMSWVRQAPGKGLEWVSGITGSGGSTYYADSV
KGRFTISRDNSKNTLYLQMNSLRAEDTAVYYCAKDPSATVLMSWFDPWGQGTLVTVSSASTKGP
SVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEALHNHYTQKSLSLSPGK

FIG. 2

Denosumab LC sequence (SEQ ID NO:2):

EIVITQSPGTLSLSPGERATLSCRASQSVRGRYLAWYQQKPGQAPRILLYGASSRATGLPDRFS
GSGSGTDFTLTISRNKPEDFAVFYCQQYGSSPRTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKV
YACEVTHQGLSSPVTKSFNRGEC

Table 1

| Parameter # | Parameter Category | Parameter | Reference Criterion (rule) |
|---|---|---|---|
| | | ○ Mannose, ◁ Fucose, □ GlcNAc, ⊘ Galactose, ◇ Sialic Acid | |
| 1 | HM5 | [Structure diagram] | >8.00%* |
| 2 | HM6 | [Structure diagram] | >0.25%* |
| 3 | Complex G0F | [Structure diagram with α6, α3, β4, β4, β – 2AB] | >50.00%* |
| 4 | Complex G1F | [Structure diagram with α6, α3, β4, β4, β – 2AB] | <12.00%* |
| 5 | Complex G1F | [Structure diagram with β2, α6, α3, β4, β4, β, α6, β2 – 2AB] | >8.50%* |
| 6 | Complex | [Structure diagram with α6, α3, β4, β4, β, α6 – 2AB] | >1.30%* |
| 7 | Complex G2F | [Structure diagram] | <2.60%* |
| 8 | Complex | [Structure diagram] | >1.20%* |
| 9 | Complex | [Structure diagram] | >0.25%* |
| 10 | Hybrid | [Structure diagram] | >0.10%* |
| 11 | C-terminal-lysine | Amount of lysine present at the C-terminus of the heavy chain | <5.00%$ |
| 12 | HC-pyroglu | Pyroglutamate (pyroglu) at the N-terminus of the heavy chain | <10.00%# |
| 13 | LC-pyroglu | Pyroglutamate at the N-terminus of the light chain | <3.00%# |
| 14 | HC-M256-Sulfo | Post-transitional modification of the M256 residue (Kabat et al. numbering) of the heavy chain - residue is oxidized to form methionine sulfoxide | >4.00%# |
| 15 | LC-D17-Suc | Succinimide formation at aspartic acid 17 on the light chain | <0.05%# |

FIG. 3

METHODS RELATED TO DENOSUMAB

This application is a national stage application under 35 U.S.C. §371 of PCT Application No.: PCT/US2013/043674, filed May 31, 2013, which claims the benefit of U.S. Provisional Application No. 61/654,515, filed Jun. 1, 2012; and U.S. Provisional Application 61/783,013, filed Mar. 14, 2013.

This disclosure provides compositions and methods related to denosumab.

BACKGROUND OF THE INVENTION

Denosumab (Prolia®) is a human IgG2 monoclonal antibody with affinity and specificity for human RANKL (receptor activator of nuclear factor kappa-B ligand). Denosumab has an approximate molecular weight of 147 kD and is produced in genetically engineered mammalian (Chinese hamster ovary) cells. Prolia® is a sterile, preservative-free, clear, and colorless to pale yellow solution.

Denosumab is presently indicated for the treatment of postmenopausal women with osteoporosis at high risk for fracture; as a treatment to increase bone mass in men at high risk for fracture receiving androgen deprivation therapy for nonmetastatic prostate cancer; and as a treatment to increase bone mass in women at high risk for fracture receiving adjuvant aromatase inhibitor therapy for breast cancer (from Prolia® Prescribing Information dated September 2011, Amgen, Inc.)

SUMMARY OF THE INVENTION

The present disclosure provides, in part, methods for evaluating, identifying, and/or producing (e.g., manufacturing) denosumab. In some instances, methods herein allow highly resolved evaluation of denosumab useful for, inter alia, manufacturing denosumab, characterizing denosumab, identifying and/or confirming denosumab, monitoring the structure of denosumab, comparing denosumab preparations made over time or made under different conditions, and/or controlling the structure of denosumab.

In certain aspects, the disclosure provides methods of evaluating a glycoprotein preparation (e.g., such as a glycoprotein drug substance or drug product preparation). Such methods can include evaluating the glycoprotein preparation for the presence, absence, level and/or ratio of one or more (e.g., two or more when working with ratios) denosumab-specific parameters (i.e., acquiring information (e.g., value(s)) pertaining to the denosumab-specific parameters). Such methods can also optionally include providing, e.g., acquiring, a determination of whether the presence, absence, level and/or ratio of one or more denosumab-specific parameters evaluated meets a reference criteria for the one or more denosumab-specific parameters, which determination includes, for example, comparing the presence, absence, level and/or ratio of one or more denosumab-specific parameters evaluated with the reference criteria and/or confirming that the presence, absence, level or ratio of one or more denosumab-specific parameters evaluated has a defined (e.g., predefined) relationship with the reference criteria. In some instances, the one or more (e.g., two or more when working with ratios) denosumab-specific parameters evaluated include one or more (e.g., 1, 2, 3, 4, 5, 6, 7, 8, 9, 10, 11, 12, 13, 14, 15) parameters disclosed in Table 1.

In certain other aspects, the disclosure provides methods of manufacturing denosumab drug product, such methods include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test glycoprotein preparation (e.g., a sample of a test glycoprotein preparation), a second step of acquiring (e.g., detecting, measuring, receiving, or obtaining, as discussed subsequently herein) at least one value (e.g., 1, 2, 3, 4, 5, 6, 7, 8, 9, 10, 11, 12, 13, 14, or 15) for an denosumab parameter listed in Table 1 for the test glycoprotein preparation, and a third step of processing at least a portion of the test glycoprotein preparation (e.g., processing a portion of a manufacturing lot, batch, or run, an entire manufacturing lot, batch, or run, or multiple manufacturing lots, batches, or runs) as denosumab drug product (e.g., in a form or packaging intended for marketing or administration as described subsequently herein) if the at least one value for the test glycoprotein preparation meets a reference criterion shown in Table 1 for the parameter, thereby manufacturing denosumab drug product. In some instances, the second step of such methods includes acquiring values for any combination of two or more denosumab parameters listed in Table 1, and the third step of such methods includes processing at least a portion of the test glycoprotein preparation as denosumab drug product if the values for the any combination of two or more denosumab parameters for the test glycoprotein preparation meet the corresponding reference criterion shown in Table 1 for the parameters. In some instances, the any combination of two or more denosumab parameters can include 2, 3, 4, 5, 6, 7, 8, 9, 10, 11, 12, 13, 14, or 15 of the denosumab parameters listed in Table 1 and/or any two or more of parameter numbers 1, 2, 3, 4, 5, 6, 7, 8, 9, 10, 11, 12, 13, 14, and/or 15 shown in Table 1. In some instances, the second step of such methods includes acquiring a value for a plurality of denosumab parameters listed in Table 1, and the third step of such methods includes processing at least a portion of the test glycoprotein preparation as denosumab drug product if the value for the plurality for the test glycoprotein preparation meets the corresponding reference criterion shown in Table 1 for the parameters. In some instances, the plurality includes 2, 3, 4, 5, 6, 7, 8, 9, 10, 11, 12, 13, 14, or 15 of the denosumab parameters listed in Table 1 and/or parameter numbers 1, 2, 3, 4, 5, 6, 7, 8, 9, 10, 11, 12, 13, 14 and/or 15 shown in Table 1. In some instances, the second step of such methods includes acquiring a value for at least one value of denosumab parameters listed in Table 1, and the third step of such methods includes processing at least a portion of the test glycoprotein preparation as denosumab drug product if at least one of the at least one value for the plurality for the test glycoprotein preparation meets the corresponding reference criterion shown in Table 1 for the parameter.

In some instances, the test glycoprotein preparation obtained or produced in the first step of such methods includes a recombinant antibody composition having a first amino acid sequence with at least 85% identity to SEQ ID NO:1 (e.g., 90, 95, 98, or 100% identity to SEQ ID NO:1) and a second amino acid sequence with at least 85% identity to SEQ ID NO:2 (e.g., 90, 95, 98, or 100% identity to SEQ ID NO:2). In some instances, the recombinant antibody composition includes a first amino acid sequence with 100% identity to SEQ ID NO:1 and a second amino acid sequence with 100% identity to SEQ ID NO:2. In either instance, the first and second amino acid sequence combine when expressed to form the recombinant antibody in which the first sequence is the antibody heavy chain and the second sequence is the antibody light chain. In some instances, evaluation methods include, for a glycoprotein preparation, evaluating information (e.g., value(s)) pertaining to one or more denosumab-specific parameters and, optionally, providing, e.g., acquiring, a determination of whether the information meets a denosumab signature, e.g., by comparing the information with the denosumab signature and/or confirming that the information has a defined (e.g., predefined) relationship with the denosumab signature.

In some instances, evaluation methods include, for a glycoprotein preparation, evaluating information (e.g., value(s)) pertaining to one or more of the denosumab parameters disclosed in Table 1, and, optionally, providing, e.g., acquiring, a determination of whether the information meets a denosumab signature, e.g., by comparing the information with the denosumab signature and/or confirming that the information has a defined (e.g., predefined) relationship with the denosumab signature. For example, for a given glycoprotein preparation, methods can include: evaluating HM5 and obtaining a value therefor, and, optionally, determining whether the value conforms to the reference criterion for HM5 provided in Table 1, wherein, in this example, the reference criterion for HM5 is a denosumab signature. In this instance, the value for HM5 would conform to the denosumab signature if it is greater than 8.00.

In another aspect, the disclosure provides methods of identifying a test glycoprotein preparation (e.g., such as a glycoprotein drug substance or drug product preparation) as denosumab. In some instances, identification methods include, for a glycoprotein preparation, evaluating information (e.g., value(s)) pertaining to one or more denosumab-specific parameters, providing, e.g., acquiring, a determination of whether the information meets a denosumab signature, e.g., by comparing the information with the denosumab signature and/or confirming that the information has a defined (e.g., predefined) relationship with the denosumab signature, and identifying the glycoprotein preparation as denosumab if the information meets the denosumab signature.

In some instances, identification methods include, for a glycoprotein preparation, evaluating information (e.g., value(s)) pertaining to one or more of the 'denosumab parameters' disclosed in Table 1, providing, e.g., acquiring, a determination of whether the information meets a denosumab signature, e.g., by comparing the information with the denosumab signature and/or confirming that the information has a defined (e.g., predefined) relationship with the denosumab signature, and identifying the glycoprotein preparation as denosumab if the acquired information meets the denosumab signature. For example, for a given glycoprotein preparation, methods can include: evaluating HM5 and obtaining a value therefor, determining whether the value conforms to the reference criterion for HM5 provided in Table 1, and identifying the glycoprotein preparation as denosumab if the information conforms, wherein, in this example, the reference criterion for HM5 is a denosumab signature. In this instance, the value for HM5 would conform to the denosumab signature if it is greater than 8.00.

In a further aspect, the disclosure provides methods of producing (e.g., manufacturing) denosumab (e.g., denosumab drug product). In some instances, production methods include, for a glycoprotein preparation, evaluating information (e.g., value(s)) pertaining to one or more denosumab-specific parameters, providing, e.g., acquiring, a determination of whether the information meets a denosumab signature, e.g., by comparing the information with the denosumab signature and/or confirming that the information has a defined (e.g., predefined) relationship with the denosumab signature, and processing the glycoprotein preparation (e.g., as denosumab drug product) if the information meets the denosumab signature, thereby producing denosumab (e.g., denosumab drug product).

In some instances, production methods include, for a glycoprotein preparation, evaluating information (e.g., value(s)) pertaining to one or more denosumab parameters disclosed in Table 1, providing, e.g., acquiring, a determination of whether the information meets a denosumab signature, e.g., by comparing the information with the denosumab signature and/or confirming that the information has a defined (e.g., predefined) relationship with the denosumab signature, and processing the glycoprotein preparation (e.g., as denosumab drug product) if the information meets the denosumab signature, thereby producing denosumab (e.g., denosumab drug product). For example, for a given glycoprotein preparation, production methods can include: evaluating a value for HM5 for the glycoprotein preparation, comparing the value with the reference criterion for HM5 provided in Table 1, determining whether the value obtained meets with the reference value for HM5, and processing the glycoprotein preparation as denosumab drug product if the value obtained meets the reference criterion for HM5, wherein, in this example, the reference criterion for HM5 is a denosumab signature. In this instance, the value for HM5 would conform to the reference criterion for HM5 if it is greater than 8.00. In some instances, these methods can further include packaging, labeling, and/or shipping the denosumab drug product, e.g., as discussed in further detail herein.

As used herein, a denosumab signature comprises a plurality of reference criteria or rules for a plurality of parameters that define denosumab. In some instances, a denosumab signature can be a pharmaceutical specification, a commercial product release specification, a product acceptance criterion, a pharmacopeial standard, or a product labeling description. In some instances, the denosumab signature comprises a plurality of reference criteria or rules for a plurality of parameters shown in Table 1 (FIG. 3).

While the present disclosure provides exemplary units and methods for the evaluation, identification, and production methods disclosed herein (see, e.g., Tables 1 and 2), a person of ordinary skill in the art will appreciate that performance of the evaluation, identification, and production methods herein is not limited to use of those units and/or methods. For example, denosumab signatures described herein are generally described, for each parameter, as a value for a glycan or structure relative to total glycan on a mol/mol basis (see, e.g., Table 1). A person of skill in the art understands that although the use of other metrics or units (e.g., mass/mass, mole percent vs. weight percent) to measure a described parameter might give rise to different absolute values than those described herein, e.g., in Table 1, a test glycoprotein preparation meets a disclosed denosumab reference criterion or signature even if other units or metrics are used, as long as the test glycoprotein preparation meets the herein disclosed reference criterion or signature when the herein disclosed units and metrics are used, e.g., allowing for the sensitivity (e.g., analytical variability) of the method being used to measure the value.

Denosumab parameters shown in Table 1 are parameters that, alone, in any combination, or together, distinguish denosumab from non-denosumab glycoprotein (see below). In some instances, a denosumab parameter is part of the glycoprotein, e.g., connected with the rest of the glycoprotein by a covalent bond, i.e., an intrinsic parameter. Intrinsic parameters include the presence, absence, level, ratio (with another entity), or distribution of a physical moiety, e.g., a moiety arising from or associated with a post-translational event. Exemplary parameters include the presence (or absence), abundance, absolute or relative amount, ratio (with another entity), or distribution of a glycan, a linkage, a glycoform, or post-translationally added components of the preparation. In some instances, a parameter is not part of the glycoprotein but is present in the preparation with the glycoprotein (i.e., in a glycoprotein preparation), i.e., an extrinsic, parameter. Exemplary parameters of this type include the presence (or absence), abundance, ratio (with another entity), or distribution of, e.g., impurities, e.g., host cell proteins, residue from purification processes, viral impurities, and enclosure components.

In some instances, a denosumab signature comprises reference criteria or rules for 2, 3, 4, 5, 6, 7, 8, 9, 10, 11, 12, 13, 14, 15 or substantially all, parameters shown in Table 1. In some instances, a denosumab signature comprises reference criteria or rules for two or more (e.g., 2, 3, 4, 5, 6, 7, 8, 9, 10, 11, 12, 13, 14, or 15) of denosumab parameter(s) 1, 2, 3, 4, 5, 6, 7, 8, 9, 10, 11, 12, 13, 14, and/or 15. In some instances, an denosumab signature comprises predetermined reference criteria or rules for 2, 3, 4, 5, 6, 7, 8, 9, 10, 11, 12, 13, 14, or 15 parameters shown in Table 1. In some embodiments, predetermined reference criteria can include reference criterion or criteria for: parameter number(s) 1, 2, 6, 8 and/or 11 shown in Table 1; one or more (e.g., two, three, four or more) of parameter number(s) 1, 2, 6, 8 and/or 11 with one or more (e.g., two, three, four, five, six, seven, eight, nine or more) of parameter number(s) 3, 4, 5, 7, 9, 10, 12, 13, 14 and/or 15.

In some instances, methods (i.e., evaluation, identification, and production methods) can further include, e.g., one or more of: providing or obtaining a glycoprotein preparation (e.g., such as a glycoprotein drug substance or a precursor thereof); memorializing confirmation or identification of the glycoprotein preparation as denosumab using a recordable medium (e.g., on paper or in a computer readable medium, e.g., in a Certificate of Testing, Certificate of Analysis, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) that a glycoprotein preparation is denosumab; selecting the glycoprotein preparation for further processing (e.g., processing (e.g., formulating) the glycoprotein preparation as a drug product (e.g., a pharmaceutical product) if the glycoprotein preparation is identified as denosumab; reprocessing or disposing of the glycoprotein preparation if the glycoprotein preparation is not identified as denosumab.

In some instances, methods (i.e., evaluation, identification, and production methods) include taking action (e.g., physical action) in response to the methods disclosed herein. For example, the glycoprotein preparation is classified, selected, accepted or discarded, released or withheld, processed into a drug product, shipped, moved to a different location, formulated, labeled, packaged, released into commerce, or sold or offered for sale, depending on whether the preselected relationship is met.

In some instances, processing may include formulating, packaging (e.g., in a syringe or vial), labeling, or shipping at least a portion of the glycoprotein preparation. In some instances, processing includes formulating, packaging (e.g., in a syringe or vial), and labeling at least a portion of the glycoprotein as denosumab drug product. Processing can include directing and/or contracting another party to process as described herein.

DEFINITIONS

As used herein, a glycoprotein refers to amino acid sequences that include one or more oligosaccharide chains (e.g., glycans) covalently attached thereto. Exemplary amino acid sequences include peptides, polypeptides and proteins. Exemplary glycoproteins include glycosylated antibodies and antibody-like molecules (e.g., Fc fusion proteins). Exemplary antibodies include monoclonal antibodies and/or fragments thereof, polyclonal antibodies and/or fragments thereof, and Fc domain containing fusion proteins (e.g., fusion proteins containing the Fc region of IgG1, or a glycosylated portion thereof). A glycoprotein preparation is a composition or mixture that includes at least one glycoprotein.

A glycoprotein preparation (e.g., such as a glycoprotein drug substance or a precursor thereof) included herein is or includes a glycoprotein (e.g., an antibody) that has a first amino acid sequence with at least 85% identity to SEQ ID NO:1 and a second amino acid sequence with at least 85% identity to SEQ ID NO:2. In some instances, the first and/or second amino acid sequence(s) have at least 90%, 91%, 92%, 93%, 94%, 95%, 96%, 97%, 98%, 99%, or 100% identity to SEQ ID NO:1 and/or at least 90%, 91%, 92%, 93%, 94%, 95%, 96%, 97%, 98%, 99%, or 100% identity to SEQ ID NO:2.

In some instances, a glycoprotein preparation (e.g., such as a glycoprotein drug substance or a precursor thereof) can be a sample from a proposed or test batch of denosumab drug substance or drug product. As used herein, a batch of a glycoprotein preparation refers to a single production run of the glycoprotein. Evaluation of different batches thus means evaluation of different production runs or batches. As used herein sample(s) refer to separately procured samples. For example, evaluation of separate samples could mean evaluation of different commercially available containers or vials of the same batch or from different batches.

As used herein, denosumab is the generic, compendial, nonproprietary, or official FDA name for the product marketed as Prolia® by Amgen Inc. and a product that is interchangeable with or equivalent to the product marketed as Prolia®.

As used herein, evaluating, e.g., in the evaluation/evaluating, identifying, and/or producing aspects disclosed herein means reviewing, considering, determining, assessing, analyzing, measuring, and/or detecting the presence, absence, level, and/or ratio of one or more denosumab-specific parameters in a glycoprotein preparation to provide information pertaining to the one or more denosumab-specific parameters. In some instances, evaluating can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Evaluating can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. In some instances, evaluating a glycoprotein preparation includes detecting the presence, absence, level or ratio of one or more (e.g., two or more when working with ratios) disclosed in Table 1 using methods disclosed in Table 2.

Information (e.g., value(s)) pertaining to a denosumab-specific parameter or a denosumab parameter means information, regardless of form, that describes the presence, absence, abundance, absolute or relative amount, ratio (with another entity), or distribution of a moiety associated with the glycoprotein preparation and/or denosumab. Information is evaluated in a glycoprotein preparation as disclosed herein. Information is also conveyed in a denosumab signature. Information can be qualitative, e.g., present, absent, intermediate, or quantitative, e.g., a numerical value such as a single number, or a range, for a parameter. In some instances, information is from a single sample or batch or a plurality of samples or batches. In some instances, information can be a range or average (or other measure of central tendency), e.g., based on the values from any X samples or batches, e.g., wherein at least of the samples or batches is being evaluated for commercial release, wherein X is equal to, at least, or no more than, 2, 3, 4, 5, 6, 7, 8, 9, 10, 11, 12, 13, 14 or 15. In some instances, information can be, for example: a statistical function, e.g., an average, of a number of values; a function of another value, e.g., of the presence, distribution or amount of a second entity present in the sample, e.g., an internal standard; a statistical function, e.g., an average, of a number of values; a function of another value, e.g., of the presence, distribution or amount of a second entity present in the sample, e.g., an internal standard; a value, e.g., a qualitative value, e.g., present, absent, "below limit of detection", "within normal limits" or intermediate. In some instances, information can be a quantitative value, e.g., a numerical value such as a single number, a range of values, a "no less than x amount" value, a "no more than x amount" value. In some instances, information can be abundance. Abundance can be expressed in relative terms, e.g., abundance can be expressed in terms of the abundance of a structure in relation to another component in the preparation. E.g., abundance can be expressed as: the abundance of a structure (or a first group of structures) in Table 1 relative to the amount of protein; the abundance of a structure (or a first group of structures) in Table 1 relative to the abundance of a second structure (or second group of structures) in Table 1. Abundance, e.g., abundance of a first structure relative to another structure, can be with regard to the preparation as a whole, a single molecule, or a selected site on the protein backbone. E.g., the parameter can be the relative proportion of a first structure from Table 1 and a second structure from Table 1 at a selected site and the value can be expressed as, e.g., a proportion, ratio or percentage. Information can be expressed in any useful term or unit, e.g., in terms of weight/weight, number/number, number/weight, and weight/number. In many cases, the reference criterion is defined by a range of values.

As used herein, acquire or acquiring (e.g., acquiring information) means obtaining possession of a physical entity, or a value, e.g., a numerical value, by "directly acquiring" or "indirectly acquiring" the physical entity or value. Directly acquiring means performing a process (e.g., performing an assay or test on a sample or "analyzing a sample" as that term is defined herein) to obtain the physical entity or value. Indirectly acquiring refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are shown in Table 2.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

These, and other aspects of the invention, are described in more detail below and in the claims.

DESCRIPTION OF THE DRAWINGS

FIG. 1 | Amino acid sequence of heavy chain of denosumab (SEQ ID NO: 1).

FIG. 2 | Amino acid sequence of light chain of denosumab (SEQ ID NO:2).

FIG. 3 | Table 1 including a plurality of denosumab parameters. In Table 1, the following applies:

* For any given parameter, percent refers to the number of moles of PNGase F-released glycan X relative to total moles of PNGase F-released glycan detected as disclosed in Table 2, wherein X represents the parameter of interest (e.g., parameter(s) 1-10).

For any given parameter, percent refers to the level of modified peptide Y relative to the sum of the levels of modified peptide Y and unmodified peptide Y, detected as disclosed in Table 2, wherein Y represents the parameter of interest (e.g., parameter(s) 12-15).

$ For C-terminal-lysine, percent refers to the level of C-terminal-lysine-containing peptide relative to the sum of the levels of C-terminal-lysine-containing and C-terminal-lysine-free peptides detected as disclosed in Table 2.

DETAILED DESCRIPTION

Detailed, high resolution, structural information about Prolia® (e.g., related to the presence of signature glycan species or quantitative analyses ascribing site-specificity for backbone modifications) is useful to be able to make and test products that qualify as denosumab, e.g., that are interchangeable versions of Prolia®. Such information is also useful in monitoring product changes and controlling structural drift that may occur as a result of manufacturing changes. The art supports, however, that information necessary to be able to make and test products that qualify as denosumab, e.g., that are interchangeable versions of Prolia®, or any other branded biologic, is unavailable (see, e.g., Nowicki, "Basic Facts about Biosimilars," Kidney Blood Press. Res., 30:267-272 (2007); Hincal "An Introduction To Safety Issues In Biosimilars/Follow-On Biopharmaceuticals", J. Med. CBR Def., 7:1-18, (2009); Roger, "Biosimilars: current status and future directions," Expert Opin. Biol. Ther., 10(7):1011-1018 (2010); Schellekens et al., Nat. Biotechnol. 28:28-31 (2010); Sekhon et al., Biosimilars, 1:1-11 (2011)). One exemplary report states that "[t]he size and complexity of . . . therapeutic proteins make the production of an exact replica almost impossible; therefore, there are no true generic forms of these proteins . . . . Verification of the similarity of biosimilars to innovator medicines remains a key challenge" (Hincal, supra). This disclosure provides, in part, methods and compositions sufficient to make and test products that qualify as denosumab, e.g., that are interchangeable versions of Prolia®. Glycoprotein preparations can be obtained from any source. In some instances, providing or obtaining a glycoprotein preparation (e.g., such as a glycoprotein drug substance or a precursor thereof), e.g., that is or includes a glycoprotein, can include providing a host cell, e.g., a mammalian host cell (e.g., a CHO cell) that is genetically engineered to express a glycoprotein having an amino acid sequence at least 85% identical to SEQ ID NO:1 and an amino acid sequence at least 85% identical to SEQ ID NO:2 (e.g., a genetically engineered cell); culturing the host cell under conditions suitable to express the glycoprotein (e.g., mRNA and/or protein); and, optionally, purifying the expressed glycoproteins, e.g., in the form of a recombinant antibody) from the cultured cell, thereby producing a glycoprotein preparation. In some instances, the host cell is genetically engineered to express a glycoprotein having an amino acid sequence at least 90%, 91%, 92%, 93%, 94%, 95%, 96%, 97%, 98%, 99%, or 100% identical to SEQ ID NO:1 and an amino acid sequence at least 90%, 91%, 92%, 93%, 94%, 95%, 96%, 97%, 98%, 99%, or 100% identical to SEQ ID NO:2, wherein the expressed amino acid sequences form a recombinant antibody composition.

As used herein percent (%) sequence identity with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. (E.g., gaps can be introduced in one or both of a first and a second amino acid or nucleic acid sequence for optimal alignment and non-homologous sequences can be disregarded for comparison purposes). Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances a product will include amino acid variants, e.g., species that differ at terminal residues, e.g., at one or two terminal residues. In instances of such cases the sequence identity which is compared is the identity between the primary amino acid sequences of the most abundant active species in each of the products being compared. In some instances sequence identity refers to the amino acid sequence encoded by a nucleic acid that can be used to make the product.

In some instances, a denosumab signature disclosed herein can include 1, 2, 3, 4, 5, 6, 7, 8, 9, 10, 11, 12, 13, 14, or 15 of the denosumab parameters (e.g., the reference criterion therefor) shown in Table 1 (e.g., including any combination of 2 or more (e.g., 3, 4, 5, 6, 7, 8, 9, 10, 11, 12, 13, 14, or 15) of parameter numbers 1-15 shown in Table 1).

In some instances, a denosumab signature disclosed herein can include, other structures or characteristics (whether intrinsic or extrinsic) of denosumab, e.g., that distinguish denosumab from non-denosumab glycoprotein (see application entitled Methods of Evaluating and Making Biologics, filed on Jun. 1, 2012, as U.S. Ser. No. 61/654,467, for exemplary structures or characteristics). Examples of structures or characteristics include: the amount of GalNAc in the preparation (e.g., relative to total glycans of the preparation); the amount of truncated core glycans; the amount of aglycosylated glycans; the amount of each species of high mannose glycans; the amount of sialylated glycans or particular species of sialylated glycans; the ratio of monosialylated:diasylated glycans, the amount of diacetylated sialic acids (NeuXAc2), the amount of one or more of: NeuGc; NeuAc; Neu5,7,Ac2; Neu5Gc,9Ac; Neu5, 8Ac2; Neu5,9Ac2; Neu4,5Ac2. Examples of parameters related to the glycan linkage composition of a glycoprotein preparation can be: the presence or amount of one or more of terminal fucose; terminal mannose; terminal galactose; 2 linked mannose; 3.6 linked mannose; terminal GlcNAc; terminal GalNAc; 4 linked GlcNAc; 4,6 linked GlcNAc. A parameter may also be the ratio of one of these to another or to another property. Examples of parameters related to the glycoform composition of a glycoprotein preparation include: the absence or presence of one or more specific glycoforms (e.g., one or more glycoforms described in Table 1); the amount or abundance of a specific glycoform in the preparation relative to total glycoforms (e.g., in a w/w basis); the ratio of one particular glycoform to another. Examples of parameters related to post-translational modification in the preparation include: the absence or presence of one or more specific post-translational modification; the abundance or distribution of one or more specific post-translational modification.

In some instances, the present disclosure includes determining whether information evaluated for a glycoprotein preparation meets a denosumab signature, e.g., by comparing the information with the denosumab signature and/or confirming that the information has a defined (e.g., predefined) relationship with the denosumab signature.

In some instances, methods disclosed herein can be used to confirm the identity and/or quality of denosumab preparations. For example, methods can include assessing preparations (e.g., samples, lots, and/or batches) of a test glycoprotein to confirm whether the test glycoprotein qualifies as denosumab, and, optionally, qualifying the test protein as denosumab if qualifying criteria (e.g. predefined qualifying criteria) are met; thereby evaluating, identifying, and/or producing (e.g., manufacturing) denosumab.

Methods of the disclosure have a variety of applications and include, e.g., quality control at different stages of manufacture, analysis of denosumab preparations prior to or after completion of manufacture (e.g., prior to or after distribution to a fill/finish environment or facility), prior to or after release into commerce (e.g., before distribution to a pharmacy, a caregiver, a patient, or other end-user). Thus, the preparation can be any preparation that potentially comprises denosumab. In an embodiment the denosumab preparation is a drug substance (an active pharmaceutical ingredient or "API") or a drug product (an API formulated for use in a subject such as a human patient). In an embodiment the preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation. In an embodiment the glycoprotein preparation from an intermediate step in production, e.g., it is after secretion of the glycoprotein from a cell but prior to purification of drug substance.

Evaluations from methods of the invention are useful for guiding, controlling or implementing a number of activities or steps in the process of making, distributing, and monitoring and providing for the safe and efficacious use of denosumab. Thus, in an embodiment, e.g., responsive to the evaluation, e.g., depending on whether a criterion is met, a decision or step is taken. The method can further comprise one or both of the decision to take the step and/or carrying out the step itself. E.g., the step can comprise one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation of denosumab; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject. E.g., based on the result of the determination or whether one or more subject entities is present, or upon comparison to a reference standard, the batch from which the preparation is taken can be processed, e.g., as just described.

Methods described herein may include making a decision: (a) as to whether a preparation may be formulated into drug substance or drug product; (b) as to whether a preparation may be reprocessed (e.g., the preparation may undergo a repetition of a previous process step); or (c) that the preparation is not suitable for formulation into drug substance or drug product. In instances the method comprises: formulating as referred to in step (a), reprocessing as referred to in step (b), or rendering the preparation unusable for commercial release, e.g., by labeling it or destroying it, as referred to in step (c).

Parameter Evaluation

The amino acid sequence of the heavy chain of denosumab (Prolia®) is disclosed herein as SEQ ID NO:1. The amino acid sequence of the light chain of denosumab (Prolia®) is disclosed herein as SEQ ID NO:2.

Parameters disclosed herein can be analyzed by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a glycoprotein preparation with one or more enzymes under conditions and for a time sufficient to release one or more glycans (e.g., one or more exposed glycans). In some instances, the one or more enzymes include PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SD S-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or glycoproteins. For example, in certain instances, glycans are analyzed in accordance with the present disclosure using one or more available methods (to give but a few examples, see Anumula, *Anal. Biochem.* 350(1):1, 2006; Klein et al., *Anal. Biochem.*, 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some instances, glycans are characterized using one or more of chromatographic methods, electrophoretic methods, nuclear magnetic resonance methods, and combinations thereof.

In some instances, methods for evaluating one or more denosumab-specific parameters, e.g., in a glycoprotein preparation, e.g., one or more of denosumab parameters disclosed in Table 1 in a glycoprotein preparation are known in the art and/or are disclosed in Table 2:

antibody. The sequence of the heavy chain is shown as SEQ ID NO:1 and the sequence of the light chain is shown as SEQ ID NO:2.

Characterization of Prolia® was performed by orthogonal methods. Measurements made included use of glycan profiling, glycoform analysis, post-translational modification analysis, and analysis of other intrinsic and extrinsic structures or features. Of 113 Prolia®/denosumab structures or features that were measured or determined, 15 were determined to be denosumab parameters, i.e., parameters of denosumab that distinguish denosumab from non-denosumab antibody products. These 15 denosumab parameters and values are listed in Table 3 below for a control sample of denosumab.

TABLE 2

| Method(s) | Relevant literature | Parameter |
|---|---|---|
| C18 UPLC Mass Spec.* | Chen and Flynn, Anal. Biochem., 370: 147-161 (2007) Chen and Flynn, J. Am. Soc. Mass Spectrom., 20: 1821-1833 (2009) | Glycan(s) (e.g., N-linked glycan, exposed N-linked glycan, glycan detection, glycan identification, and characterization; site specific glycation; glycoform detection (e.g., parameters 1-10); percent glycosylation; and/or aglycoosyl) |
| Peptide LC-MS (reducing/non-reducing) | Dick et al., Biotechnol. Bioeng., 100: 1132-1143 (2008) Yan et al., J. Chrom. A., 1164: 153-161 (2007) Chelius et al., Anal. Chem., 78: 2370-2376 (2006) Miller et al., J. Pharm. Sci., 100: 2543-2550 (2011) | C-terminal lysine (e.g., parameter 11) |
| LC-MS (reducing/non-reducing/alkylated) | Dick et al., Biotechnol. Bioeng., 100: 1132-1143 (2008) Goetze et al., Glycobiol, 21: 949-959 (2011) | |
| Weak cation exchange (WCX) chromatography | Dick et al., Biotechnol. Bioeng., 100: 1132-1143 (2008) | |
| LC-MS (reducing/non-reducing/alkylated) | Dick et al., Biotechnol. Bioeng., 100: 1132-1143 (2008) Goetze et al., Glycobiol., 21: 949-959 (2011) | N-terminal pyroglu (e.g., parameters 12-13) |
| PeptideLC-MS (reducing/non-reducing) | Yan et al., J. Chrom. A., 1164: 153-161 (2007) Chelius et al., Anal. Chem., 78: 2370-2376 (2006) Miller et al., J. Pharm. Sci., 100: 2543-2550 (2011) | |
| Peptide LC-MS (reducing/non-reducing) | Yan et al., J. Chrom. A., 1164: 153-161 (2007) Xie et al., mAbs, 2: 379-394 (2010) Chelius et al., Anal. Chem., 78: 2370-2376 (2006) Miller et al., J. Pharm. Sci., 100: 2543-2550 (2011) | Non-glycosylation-relatedpeptide modifications (including, for example, sequence analysis and identification of sequence variants; oxidation; succinimide; aspartic acid; and/or site-specific aspartic acid) (e.g., parameters 14 and 15) |

Literature shown in Table 2 are hereby incorporated by reference in their entirety or, in the alternative, to the extent that they pertain to one or more of the methods disclosed in Table 2.

EXAMPLES

Example 1: Characterization of Denosumab

Prolia® sample was analyzed to determine the amino acid sequences of the heavy and light chains of the denosumab

TABLE 3

| Parameter No. | Parameter Category[2] | Value[2] |
|---|---|---|
| 1 | HM5 | 9.71 |
| 2 | HM6 | 0.31 |
| 3 | Complex G0F | 54.75 |
| 4 | Complex G1F | 8.93 |
| 5 | Complex G1F | 9.64 |

TABLE 3-continued

| Parameter No. | Parameter Category[2] | Value[2] |
|---|---|---|
| 6 | Complex | 1.81 |
| 7 | Complex G2F | 2.16 |
| 8 | Complex | 1.86 |
| 9 | Complex | 0.30 |
| 10 | Hybrid | 0.20 |
| 11 | C-terminal-lysine | 1.90 |
| 12 | HC-pyroglu | 0.60 |
| 13 | LC-pyroglu | 0.00 |
| 14 | HC-M256-Sulfo | 6.40 |
| 15 | LC-D17-Suc | 0.00 |

[1]Detailed descriptions of the structures/features of each parameter are provided in Table 1.
[2]See Table 1 for unit information.

The information (values) shown for each denosumab parameter in Table 3 were used to formulate a reference criterion or rule for each denosumab parameter (shown in Table 1).

Example 2: Qualification of Glycoprotein Preparations

The reference criterion or rules described in Table 1 were used to determine whether samples of glycoprotein preparation (samples A and B) qualify as denosumab.

Sample A was analyzed and values were obtained for each of the denosumab parameters in Table 1. The values of these parameters in sample A are presented in Table 4 below. In addition, values obtained for sample A were compared to the reference criteria for denosumab as shown in Table 4:

TABLE 4

| Parameter No. | Parameter Category[1] | Sample "A" Value | Reference Criterion[2] | Comparison of "A" Values and reference criterion |
|---|---|---|---|---|
| 1 | HM5 | 3.1 | >8.00% | |
| 2 | HM6 | 0.08 | >0.25% | |
| 3 | Complex G0F | 45.64 | >50.00% | |
| 4 | Complex G1F | 22.83 | <12.00% | |
| 5 | Complex G1F | 5.9 | >8.50% | |
| 6 | Complex | 1.07 | >1.30% | |
| 7 | Complex G2F | 3.47 | <2.60% | |
| 8 | Complex | 0.28 | >1.20% | |
| 9 | Complex | 0.15 | >0.25% | |
| 10 | Hybrid | 0.25 | >0.10% | ✓ |
| 11 | C-terminal-lysine | 45.20 | <5.00% | |
| 12 | HC-pyroglu | 100.00 | <10.00% | |
| 13 | LC-pyroglu | 70.00 | <3.00% | |
| 14 | HC-M256-Sulfo | 5.50 | >4.00% | ✓ |
| 15 | LC-D17-Suc | 0.00 | <0.05% | ✓ |

[1]Detailed descriptions of the structures/features of each parameter are provided in Table 1.
[2]See Table 1 for unit information.
✓ Illustrates that a value meets the reference criterion/rule.

Data plotted in Table 4 confirms that sample A is not denosumab, according to the methods herein. Based on these data, sample A does not meet a denosumab signature that comprises all 15 parameters and, thus, does not qualify as denosumab Sample B was analyzed and values were obtained for each of the denosumab parameters in Table 1. The values of these parameters in sample B are presented in Table 5 below. In addition, values obtained for sample B were compared to the reference criteria for denosumab as shown in Table 5:

TABLE 5

| Parameter # | Parameter Category[1] | Sample B Value | Reference Criterion[2] | Comparison of "B" Values and reference criterion |
|---|---|---|---|---|
| 1 | HM5 | 0.72 | >9.00 | |
| 2 | HM6 | 0.05 | >0.25 | |
| 3 | Complex G0F | 68.46 | >50.00 | ✓ |
| 4 | Complex G1F | 16.84 | <10.00 | |
| 5 | Complex G1F | 4.8 | >8.50 | |
| 6 | Complex | 1.28 | >1.50 | |
| 7 | Complex G2F | 2.26 | <2.50 | ✓ |
| 8 | Complex | 0.2 | >1.70 | |
| 9 | Complex | 0.03 | >0.25 | |
| 10 | Hybrid | 0.06 | >0.15 | |
| 11 | C-terminal-lysine | 1.60 | <3.00 | ✓ |
| 12 | HC-pyroglu | 2.30 | <3.00 | ✓ |
| 13 | LC-pyroglu | 0.00 | <3.00 | ✓ |
| 14 | HC-M256-Sulfo | 5.90 | >5.00 | ✓ |
| 15 | LC-D17-Suc | 0.10 | <0.05 | |

[1]Detailed descriptions of the structures/features of each parameter are provided in Table 1.
[2]See Table 1 for unit information.
✓ Illustrates that a value meets the reference criterion/rule.

Data plotted in Table 5 confirms that sample B is not denosumab, according to the methods herein. Based on these data, sample B does not meet a denosumab signature that comprises all 15 parameters and, thus, does not qualify as denosumab.

A control Prolia® sample was also analyzed and values were obtained for each of the denosumab parameters in Table 1. The values of these parameters in the control are presented in Table 6 below. In addition, values obtained for the control were compared to the reference criteria for denosumab as shown in Table 6:

TABLE 6

| Parameter No. | Parameter Category | Value | Reference Criterion[2] | Comparison of "A" Values and reference criterion |
|---|---|---|---|---|
| 1 | HM5 | 9.71 | >8.00% | ✓ |
| 2 | HM6 | 0.31 | >0.25% | ✓ |
| 3 | Complex G0F | 54.75 | >50.00% | ✓ |
| 4 | Complex G1F | 8.93 | <12.00% | ✓ |
| 5 | Complex G1F | 9.64 | >8.50% | ✓ |
| 6 | Complex | 1.81 | >1.30% | ✓ |
| 7 | Complex G2F | 2.16 | <2.60% | ✓ |
| 8 | Complex | 1.86 | >1.20% | ✓ |
| 9 | Complex | 0.3 | >0.25% | ✓ |
| 10 | Hybrid | 0.2 | >0.10% | ✓ |
| 11 | C-terminal-lysine | 1.90 | <5.00% | ✓ |
| 12 | HC-pyroglu | 0.60 | <10.00% | ✓ |
| 13 | LC-pyroglu | 0.00 | <3.00% | ✓ |

TABLE 6-continued

| Parameter No. | Parameter Category | Value | Reference Criterion[2] | Comparison of "A" Values and reference criterion |
|---|---|---|---|---|
| 14 | HC-M256-Sulfo | 6.40 | >4.00% | ✓ |
| 15 | LC-D17-Suc | 0.00 | <0.05% | ✓ |

[1]Detailed descriptions of the structures/features of each parameter are provided in Table 1.
[2]See Table 1 for unit information.
✓ Illustrates that a value meets the reference criterion/rule.

As shown in Table 6, the control Prolia® sample meets all listed reference criteria signatures for denosumab. Accordingly, the control Prolia® sample does meet a denosumab signature that includes all 15 parameters and, thus, qualifies as denosumab.

While the methods have been described in conjunction with various instances and examples, it is not intended that the methods be limited to such instances or examples. On the contrary, the methods encompass various alternatives, modifications, and equivalents, as will be appreciated by those of skill in the art.

What is claimed is:

1. A method of manufacturing a denosumab drug product, comprising:
   providing or obtaining a test glycoprotein preparation;
   acquiring a value for each of a plurality of denosumab parameters listed in Table 1 for the test glycoprotein preparation, wherein the values for the plurality of denosumab parameters distinguishes denosumab from non-denosumab glycoprotein; and wherein the plurality of denosumab parameters comprises parameters 1 and 4 listed in Table 1; and
   processing at least a portion of the test glycoprotein preparation as a denosumab drug product if the values for the plurality of denosumab parameters for the test glycoprotein preparation meet the corresponding reference criteria shown in Table 1 for the parameters, thereby manufacturing an denosumab drug product, or
   taking an alternative action if the values for the plurality of denosumab parameters for the test glycoprotein preparation do not meet the corresponding reference criteria shown in Table 1 for the parameters;
   wherein the test glycoprotein preparation comprises a recombinant antibody composition including a first polypeptide having the amino acid sequence of SEQ ID NO:1 and a second polypeptide having the amino acid sequence of SEQ ID NO:2, and wherein the first and second polypeptides together form a recombinant antibody.

2. The method of claim 1, wherein the plurality comprises: 3, 4, 5, 6, 7, 8, 9, 10, 11, 12, 13, 14, or 15 of the denosumab parameters listed in Table 1.

3. The method of claim 1, wherein the value is directly acquired by performing an analytical test on the test glycoprotein preparation.

4. The method of claim 3, wherein the value is directly acquired using C18 UPLC mass spectrometry.

5. The method of claim 1, wherein the processing step comprises combining the test glycoprotein preparation with an excipient or buffer.

6. The method of claim 1, wherein the processing step comprises one or more of: formulating test glycoprotein preparation; combining the test glycoprotein preparation with a second component; changing the concentration of the recombinant antibody composition in the test glycoprotein preparation; lyophilizing the test glycoprotein preparation; combining a first and a second aliquot of the test glycoprotein preparation to provide a third, larger, aliquot; dividing the test glycoprotein preparation into smaller aliquots; disposing the test glycoprotein preparation into a container; packaging the test glycoprotein preparation; associating a container comprising the test glycoprotein preparation with a label shipping or moving the test glycoprotein preparation to a different location.

7. The method of claim 1, wherein the denosumab drug product is approved under Section 351(k) of the Public Health Service (PHS) Act.

8. The method of claim 1, wherein the denosumab drug product is not approved under biologics license application (BLA) under Section 351(a) of the Public Health Service (PHS) Act.

9. The method of claim 1, wherein the value for at least one denosumab parameter for the test glycoprotein preparation comprises an average of values or a range of values for the parameter for multiple batches or samples of the test glycoprotein preparation.

10. The method of claim 1, wherein the plurality of reference criteria shown in Table 1 are a specification for commercial release.

11. The method of claim 1, wherein the values for a plurality of denosumab parameters are acquired for one or more samples or batches of the test glycoprotein preparation.

12. The method of claim 1, comprising:
    providing a host cell that is genetically engineered to express the first and second polypeptides,
    culturing the host cell under conditions that allow the cell to express the first and second polypeptides and form recombinant antibodies,
    harvesting the recombinant antibodies from the host cell culture to produce the test glycoprotein preparation.

13. The method of claim 1, wherein the plurality of denosumab parameters further comprise parameter numbers 2, 3, 5, 6, 7, 8, 9, 10, 11, 12, 13, 14, and/or 15 shown in Table 1.

14. The method of claim 1, wherein the denosumab drug product is an interchangeable version, under Section 351(k) of the Public Health Services (PHS) Act, of a denosumab product approved by the FDA.

15. The method of claim 1, wherein the plurality of the reference criteria is a product acceptance criterion.

16. The method of claim 1, further comprising comparing each of the acquired values of the plurality of denosumab parameters to the corresponding reference criterion shown in Table 1.

17. The method of claim 1, wherein taking an alternative action comprises (a) reprocessing, (b) disposing of, or (c) rendering the test glycoprotein preparation unusable for commercial release by labeling or destroying it.

18. The method of claim 1, wherein the processing step comprises formulating the test glycoprotein preparation.

19. The method of claim 1, wherein the processing step comprises combining the test glycoprotein preparation with a second component.

20. The method of claim 1, wherein the processing step comprises lyophilizing the test glycoprotein preparation.

* * * * *

SEQUENCE LISTING

```
<160> NUMBER OF SEQ ID NOS: 2

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ser Ala Thr Val Leu Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Phe Arg Val Val
            290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
            325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445

<210> SEQ ID NO 2
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Ile Thr Gln Ser Pro Gly Thr Leu Ser Leu Ser Pro Gly
1               5                   10                  15
Glu Arg Ala Thr Leu Ser Cys Arg Ala Ser Gln Ser Val Arg Gly Arg
            20                  25                  30
Tyr Leu Ala Trp Tyr Gln Gln Lys Pro Gly Gln Ala Pro Arg Ile Leu
            35                  40                  45
Leu Tyr Gly Ala Ser Ser Arg Ala Thr Gly Leu Pro Asp Arg Phe Ser
        50                  55                  60
Gly Ser Gly Ser Gly Thr Asp Phe Thr Leu Thr Ile Ser Arg Asn Lys
65                  70                  75                  80
Pro Glu Asp Phe Ala Val Phe Tyr Cys Gln Gln Tyr Gly Ser Ser Pro
            85                  90                  95
Arg Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
            165                 170                 175
```

-continued

```
Ser Ser Thr Leu Thr Leu Ser Lys Ala Asp Tyr Glu Lys His Lys Val
            180             185                 190

Tyr Ala Cys Glu Val Thr His Gln Gly Leu Ser Ser Pro Val Thr Lys
        195             200                 205

Ser Phe Asn Arg Gly Glu Cys
    210             215
```